United States Patent
Golba, Jr.

[11] Patent Number: 5,919,172
[45] Date of Patent: Jul. 6, 1999

[54] HYPODERMIC NEEDLE HAVING A DIFFERENTIAL SURFACE FINISH

[75] Inventor: Joseph C. Golba, Jr., Chapel Hill, N.C.

[73] Assignee: Becton, Dickinson and Company, Franklin Lakes, N.J.

[21] Appl. No.: 08/682,249

[22] Filed: Jul. 17, 1996

[51] Int. Cl.⁶ ........................................ A61M 5/32
[52] U.S. Cl. .......................... 604/272; 604/164; 604/231
[58] Field of Search .................... 604/164, 165, 604/171, 172, 199, 231, 272, 265

[56] References Cited

U.S. PATENT DOCUMENTS 4,869,259  9/1989  Elkins ........................................ 604/272

OTHER PUBLICATIONS

Anesth. Analg.: 63, pp. 1048–1049, The Lee Modification of the Tuohy Needle . . .

Primary Examiner—Michael Buiz
Assistant Examiner—Daphna Shai
Attorney, Agent, or Firm—Arthur D. Dawson

[57] ABSTRACT

A hypodermic needle of the present invention includes an elongate hollow tube with a proximal end, a distal end and has a bore therethrough. The proximal end of the needle of the invention has a hub fixedly attached thereto to connect the needle releasably to a fluid handling device with the distal end having a point for facilitating penetration of the needle into a patient's tissue. The outside surface of the tube has a proximal portion with a lower coefficient of sliding friction with the patient's tissue than the coefficient of sliding friction with the patient's tissue than a distal portion of the outside surface of the tube. The higher coefficient of friction of the distal portion enables a practitioner to substantially discriminate the needle's penetration of structures in the patient's tissue while the lower coefficient of friction proximal portion substantially reduces drag force for passage of the proximal portion through the structures already penetrated by the distal portion.

19 Claims, 4 Drawing Sheets

HYPODERMIC NEEDLE HAVING A DIFFERENTIAL SURFACE FINISH

FIELD OF THE INVENTION

This invention generally relates to administration of medicaments to patients and more particularly to hypodermic needles having an exterior surface with a differential coefficient of sliding friction with a patient's tissue.

BACKGROUND

Hypodermic needles are widely used in delivering and withdrawing fluids in medical practice. As originally used, hypodermic needles were used many times, being resterilized between usages. A practitioner would sharpen the needles when they became dull, and then sterilize them prior to the next usage. Since the needles were reused, and often may have needed sharpening, the presence or absence of any lubrication on the outer surface of the needle had little effect on the penetration force or the pain perceived by the patient who was the recipient of the needle. With the development of commercially manufactured disposable needles that always have a fresh well-sharpened point, there was recognition that lubrication of the needle substantially reduced the pain perceived by the patient when a needle was administered to them. A convention is followed in this disclosure wherein the portion of a device toward the practitioner is termed proximal and the portion of the device toward the patient is termed distal.

A tissue penetration by a hypodermic needle involves a sequence of events that collectively are perceived by the patient as whether or not the penetration caused pain. A needle first touches the skin surface, stretches it, the point then cuts into the surface and begins penetration into the tissue. As the shaft of the needle passes through the original cut and into the tissue, there is also sliding friction of the tissue against the needle surface. In the hypodermic needle art when the forces for performing a hypodermic needle penetration are measured, the force measured prior to the needle point cutting the tissue is termed the "peak penetration force" and the force required to continue the penetration into the tissue is called the "drag force." One primary component of the drag force is the sliding friction of the tissue against the surface of the needle shaft. When a subcutaneous or intra-muscular penetration is made with a hypodermic needle, the penetration depth is generally between about 0.5 cm to about 2.5 cm into the patient's tissue. As a result, the practitioner generally does not generally perceive differences in the needle point's penetration of layers. Additionally, most subcutaneous and intra-muscular hypodermic penetrations are made at a relatively high rate (20 cm to 25 cm per second) and utilize the full length of the needle. The rapid penetration rate additionally reduces any perception of layers. The use of lubricant on the surface of hypodermic needles in combination with very well sharpened needles also significantly reduces both the peak penetration force and the drag force. When the reductions by lubrication of the peak penetration force and the drag force of the needle are coupled with the short duration resultant from the high penetration rate, a patient's perception of the painfulness of the penetration is generally significantly reduced. As a result, almost all single-use sterile disposable needles are supplied with a lubricant already applied to substantially the entire needle outside surface. A concomitant effect of the reduction in the peak penetration force and the drag force by lubrication of the needle is a substantial reduction of any ability of a practitioner to discern discrete movement of the needle point through the layers of the tissue.

Hypodermic penetrations are made into the spinal column for the withdrawal of fluid and administration of medicaments, often to induce anesthesia. These spinal penetrations generally utilize needles from about 5 cm to about 9 cm long and the exact penetration depth is critical to the success of the procedure. A commonly practiced technique that requires a hypodermic penetration is delivery of a medicament, generally an anesthetic agent, into the epidural space. When an anesthetic agent is used, this technique results in a regional block anesthesia often referred to as an "epidural." The procedure is recognized by practitioners as being technique sensitive, because the patients are different physical size and a penetration beyond the epidural space and through the dural membrane with or without delivery of the anesthetic agent into the subarachnoid space may result in undesirable consequences. These undesirable consequences can include severe headaches in the postoperative period. Additionally, if the misplacement of the needle is not recognized immediately and a sufficient quantity of anesthetic agent is administered into the subarachnoid space, total spinal block, a potentially life-threatening complication, may result.

Practitioners have developed many ways to determine the placement of the needle in the epidural space. Epidural needles are often supplied with depth markings. Techniques are practiced to identify the epidural space by the loss of resistance to injection of fluid in a syringe coupled to the epidural needle. Another widely practiced technique is the modified drip method, involving an infusion tubing partially filled with normal saline attached to the epidural needle. A technique of hanging a drop of saline on the needle hub is also widely practiced. Any placement of a needle into the spine of a patient is very sensitive to the experience and skill of the practitioner. Epidural needles are generally introduced in the midline at either the lumbar (L) 2-L3 or L3–4 intervertebral space. The needle is slowly and carefully advanced into the skin, encountering subcutaneous tissue, supraspinous ligament and interspinous ligament, then entering the epidural space. The epidural needle is generally used with a stylet occluding the bore of the needle to prevent particles of tissue from being collected in the needle bore and transported into the epidural space with the delivery of the anesthetic agent. The stylet is removed to introduce the anesthetic agent through the needle.

Epidural needles are a notable exception to the general usage of lubricants on commercially available single-use needles, being supplied "dry" or unlubricated. Since the presence of lubricant on the surface of a needle significantly reduces the peak penetration force, if an epidural needle was lubricated at the distal end, the practitioner's ability to perceive the penetrations of the several structures in the tissue, i.e., the skin, subcutaneous tissue, supraspinous ligament and interspinous ligament, is substantially reduced. While the unlubricated needle improves the perception of the needle point penetration through the tissue structures, drag force on the shaft of the needle becomes more significant as the penetration depth increases and, when stick/slip friction is present, the practitioner may not be able to readily determine when the needle point has entered the epidural space.

SUMMARY

A hypodermic needle of the present invention includes an elongate hollow tube with a proximal end, a distal end having a point and has a bore therethrough. The proximal end of the needle of the invention has a hub attached thereto to connect the needle releasably to a fluid handling device. The outside surface of the tube has a proximal portion and a distal portion. The distal portion has a higher coefficient of sliding friction with a patient's tissue than the coefficient of sliding friction between the proximal portion and the patient's tissue. The distal portion enables a practitioner to substantially discriminate the needle's penetration of structures in the patient's tissue while the proximal portion with substantially reduces drag force for passage of the proximal portion through the structures already penetrated by the distal portion.

The hypodermic needle of the invention is particularly well suited for anesthetic administration into the epidural space. Correct placement of a needle into the epidural space by a practitioner is generally recognized as one of the most technique sensitive of widely practiced medical procedures. The hypodermic needle of the invention maximizes the practitioner's ability to discern the passage of the needle through the structures present in the patient's tissue by allowing him to feel the peak penetration forces as the point encounters the structure and minimizes drag forces, particularly stick/slip friction, of the shaft of the needle as it passes through the tissue. The hypodermic needle of the invention is well suited for any other penetration depth sensitive applications such as biopsy needles and the like.

DETAILED DESCRIPTION

Figure 1:
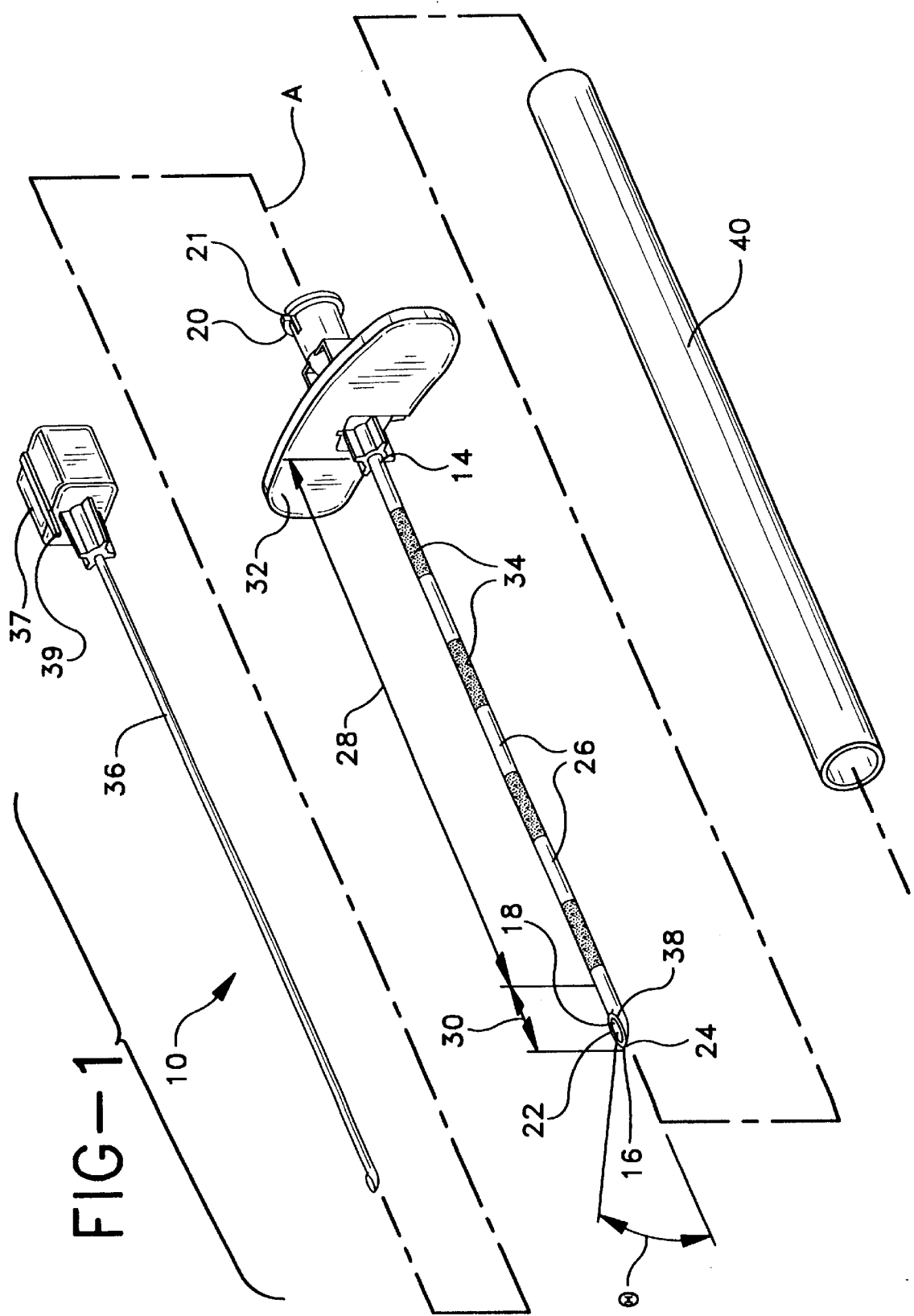
FIG. 1 is an exploded perspective view of the preferred epidural needle of the present invention.

While this invention is satisfied by embodiments in many different forms, there is shown in the drawings and is herein described in detail, a preferred embodiment of the invention with the understanding that the present disclosure is to be considered exemplary of the principles of the invention and is not considered to limit the invention to the embodiment illustrated. The scope of the invention is measured by the appended claims and their equivalents.

Figure 2:
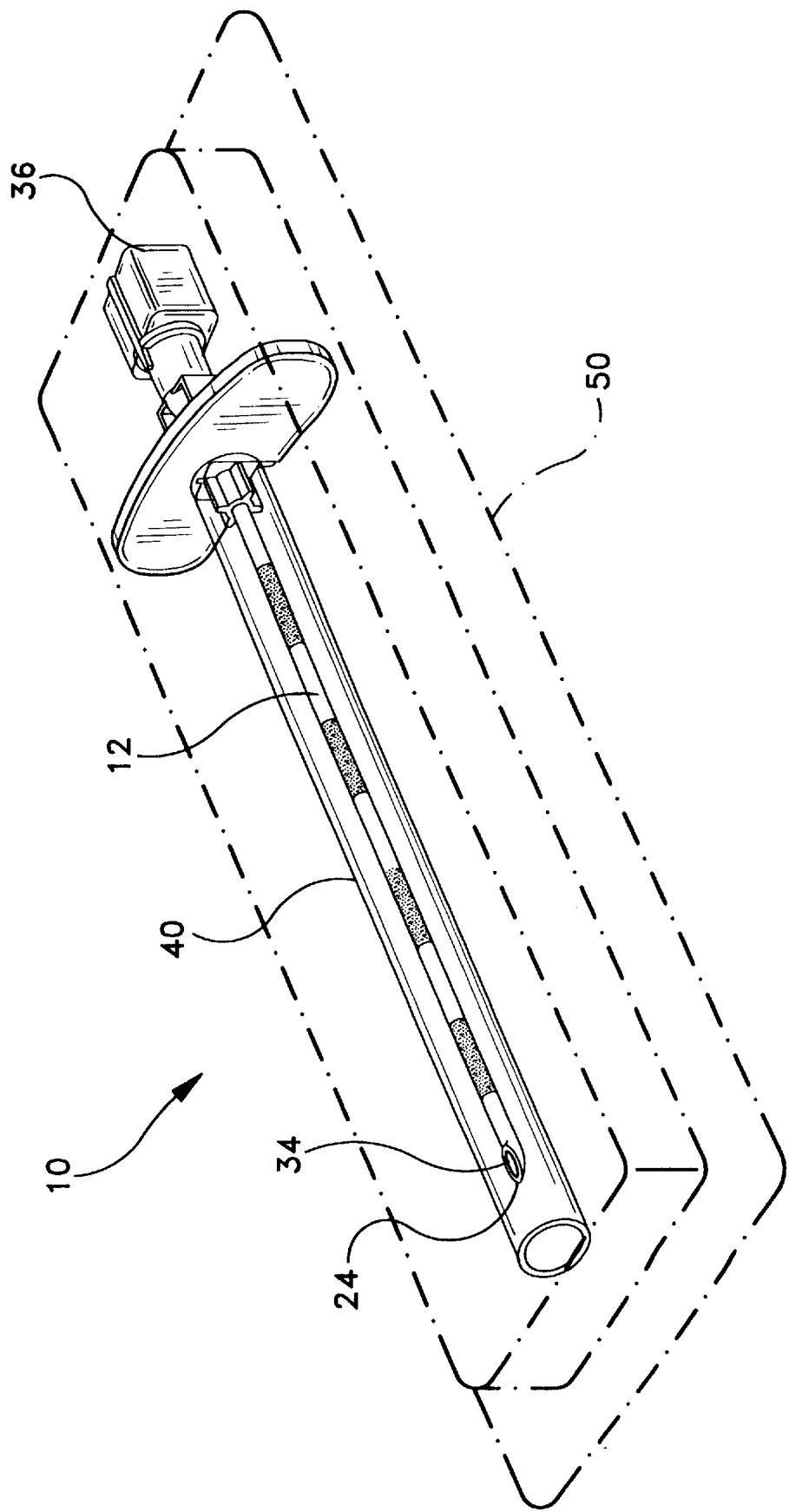
FIG. 2 is a perspective view of the invention of FIG. 1 as assembled and placed in a package.

Referring to FIGS. 1 and 2, a preferred hypodermic epidural needle 10 of the present invention includes an elongate hollow tube 12 with a longitudinal axis A. Tube 12 has a proximal end 14, a distal end 16 and a bore 18 therethrough. Proximal end 14 has a hub 20 fixedly attached thereto to releasably connect needle 10 to a fluid handling device such as a catheter, a syringe or the like. Preferably, distal end 16 has a substantially oval opening 22, into bore 18 at an angle θ to axis A to form a sharp distal point 24 to facilitate penetration of needle 10 into a patient's tissue. For the preferred epidural needle, angle θ is between about fifteen and about sixty degrees and preferably is about thirty degrees. For particular applications needle 10 may have points with other configurations and angles and be considered within the scope of the invention.

Tube 12 has an outside surface 26 with a lubricated proximal portion 28 and an unlubricated distal portion 30. Preferably distal portion 30 is between about one to about forty percent of outside surface 26 and proximal portion 28 is between about ninety-nine to about sixty percent of outside surface 26. More preferably, distal portion 30 is about ten percent of outside surface 26 and proximal portion 28 is about ninety percent of the outside surface. Additionally, since in many procedures, the entire length of the needle is not utilized, it is not necessary that the proximal portion of the needle be coated all the way to the hub, for particular applications, needles with only a partially treated proximal portion are considered within the purview of the invention. Unlubricated distal portion 30 enables a practitioner to substantially discriminate penetration of distal point 24 of the needle through structures in the patient's tissue and lubricated proximal portion 28 substantially reduces a drag force for passage of the proximal portion through the structures already penetrated thereby making the structure penetration by the distal portion the predominate perception by the practitioner, thus enhancing the practitioner's ability to discriminate the passage of the distal portion into the desired location.

Preferably, hub 20 of the epidural needle of the invention has a removable flange 32 that is positioned substantially normal to the needle's longitudinal axis to facilitate the practitioner's manipulation of the needle. The preferred epidural needle of the invention has hollow tube 12 formed from stainless steel. Tube 12 preferably has a length between about five to about ten centimeters and an outside diameter between about 0.7 mm to about 1.5 mm. Preferably, tube 12 has a plurality of graduation markings 34 for observation by the practitioner during penetration as an indication of the depth of the needle penetration.

Needle 10 is preferably supplied with a removable stylet 36 that forms a substantially continuous surface with a surface 38 of oval opening 22. Preferred stylet 36 includes a hub 37 with a key 39 configured to engage a slot 21 in needle hub 20 to substantially orient the stylet with surface 38 of the oval opening. Stylet 36 is used to occlude bore 18 during the penetration of the patient's tissue to substantially prevent accumulation of tissue fragments in bore 18 that would be transported into the epidural space when the anesthetic agent is introduced. When the practitioner has properly placed the needle in the epidural space, stylet 36 is removed and a fluid handling device, such as a syringe, is attached to the hub for introduction of the medicament, generally an anesthetic agent.

Figure 3:
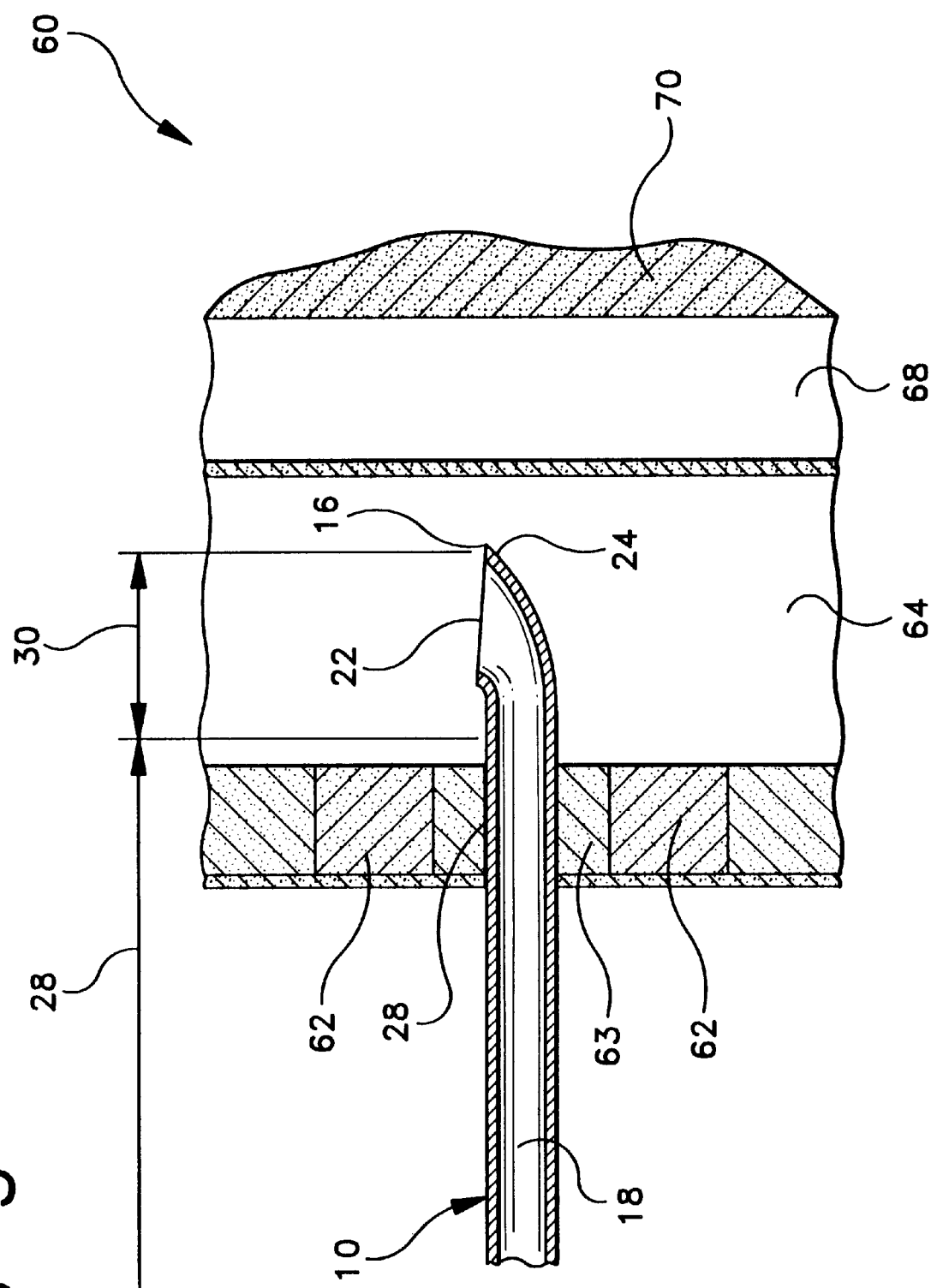
FIG. 3 is a schematic vertical cross-sectional view of the lumbar region of a human spine.
Figure 4:
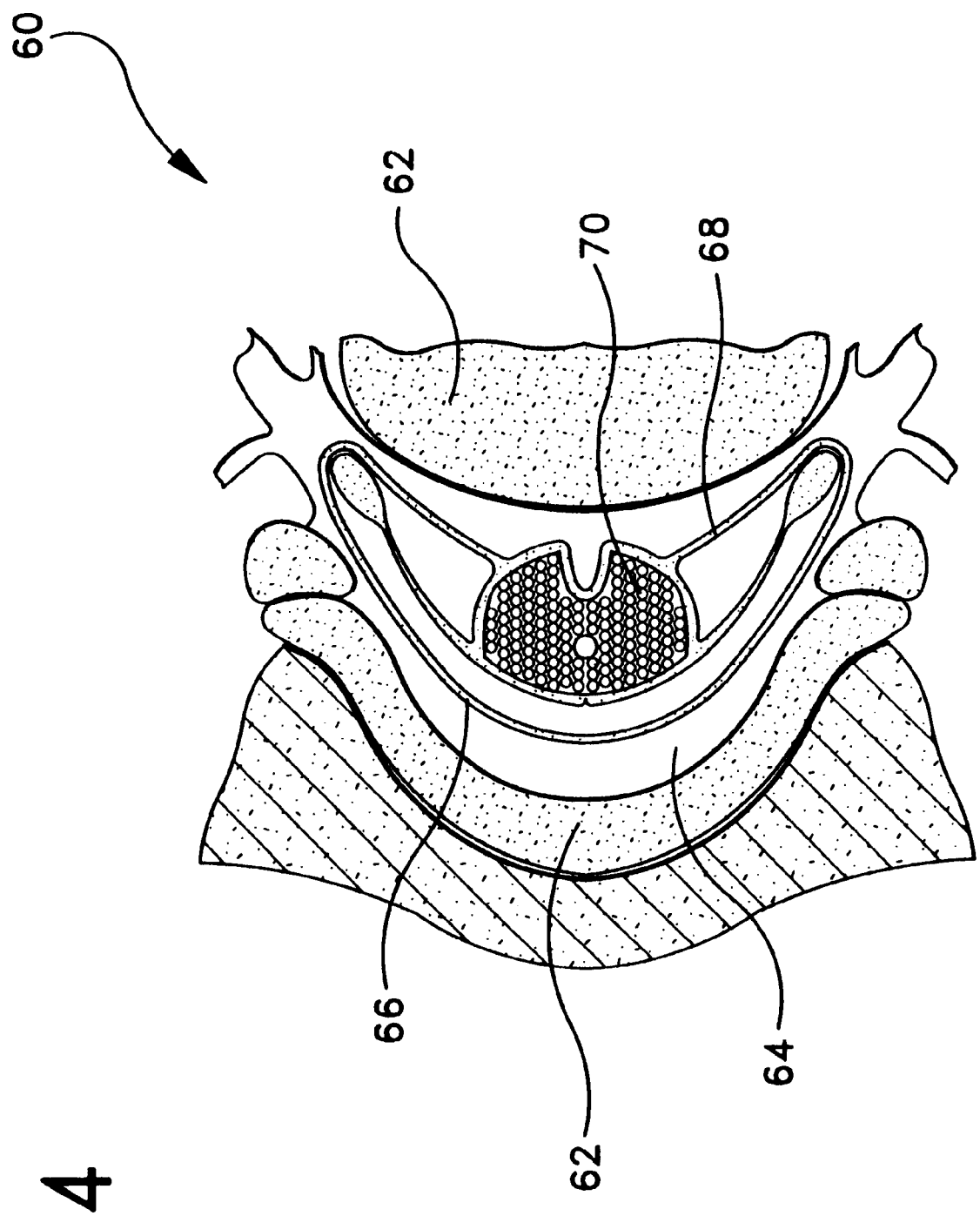
FIG. 4 is a schematic horizontal cross-sectional view of the lumbar region of a human spine.

Referring to FIGS. 3 and 4, schematic vertical and horizontal cross-sectional views of a human spine 60 show the structures encountered in placement of epidural needle 10 in the human spine. In FIG. 3, needle 10 is positioned in spine 60, between two vertebrae 62 by passing through a ligamentous tissue 63 so that distal portion 30 with distal end 16, opening 22 and distal end 24 are in the epidural space 64. When making an epidural placement, the practitioner must not penetrate through the dural membrane 66 into the subarachnoid space 68 or into the cauda equina 70. FIG. 4 schematically illustrates spine 60 in horizontal cross-section to assist the understanding of the location of vertebrae 62, epidural space 64 relative to dural membrane 66, subarachnoid space 68 and cauda equina 70. In a paper by C. E. Pither, in Anesth. Analg.: 63, 1984, pp. 1048–49, reference is made to a basic description of placing an epidural needle in the lumbar space by J. A. Lee in Anesthesia 1960: 15: 186. According to Lee, "When inserting the needle in the lumbar region, one can advance it, in patients of average build, for a distance of 3 cm without fear of missing the extra dural space or of puncturing the dura . . . From this point onwards, care must be taken. Similarly, if the extra dural space has not been located when the point has been inserted 6 cm, one is well advised to withdraw and try again at a different angle." In the paper, Pither advocates the utility of placing markings indicating the depth of placement on the surface of the needle.

Preferably, needle 10 with stylet 36 installed in the bore is covered with a shield 40 and placed in a sealed package 50, indicated in phantom in FIG. 2. Preferably, package 50 is formed from materials substantially resistant to the passage of microorganisms and exposed to conditions capable of rendering any microorganisms therein substantially non-viable. Suitable materials for forming package 50 include, but are not limited to, paper, non-woven polyolefin, thermoplastic film and the like. Suitable conditions for rendering microorganisms non-viable include exposure to ionizing radiation such as gamma radiation, electron beams and the like; and chemical sterilants such as ethylene oxide and the like.

Several examples of coatings and methods for their application to the proximal portions of needles are given below. These examples are intended to be illustrative, and not limitative of the differentially lubricated needle of the present invention. Many other needle gauge sizes, point configurations, lengths, lubricated portion/unlubricated portion ratios and lubricants may be preferred for particular applications and are considered to be within the scope of the invention. The needles used in the examples are epidural needles, other hypodermic needles for many other applications such as biopsy, radiopacity agent delivery and the like would be suitable for the present invention and are considered within the scope of the invention. Most materials suitable for use in medical device applications as a lubricant are presumed satisfactory for use in the present invention. A suitable lubricant material is a material that, when applied to a needle, reduces the coefficient of sliding friction between the surface of the needle and a patient's tissue below the coefficient of sliding friction between the unlubricated needle and the patient's tissue. Similarly, other techniques for reducing the coefficient of sliding friction with a patient's tissue of a portion of an needle including, but not limited to, mechanical surface polish applied to a portion of the surface, electropolish of a portion of a surface, differential surface finish obtained by masking, electrolytic application and selective removal of a portion of a coating, application and mechanical removal of a portion of a coating and the like are considered to be within the scope of the present invention.

Suitable polytetrafluoroethylene materials are available under the trade names Teflon™, (DuPont), Fluon™ (ICI) and Halar™ (Allied). Suitable silicone lubricants are available from Dow-Corning, General Electric, Union Carbide and others. In the examples, the polytetrafluoroethylene suspension is formed with Teflon™ 852-200 available from E. I. DuPont, Wilmington, Del. Many other PTFE suspensions are available and are considered within the scope of the present invention. Other coatings such as methyl cellulose ethers, polyvinylpyrollidone, PTFE modified nickel and the like are lubricative and are considered within the scope of the invention. Similarly, other techniques for application of coating including, but not limited to, vacuum deposition, vacuum sputtering, spraying, plasma discharge and the like are suitable for application of coatings and are considered within the scope of the invention.

In the examples, the polydimethylsiloxane and the curing silicone were selected from the DC-200™ series of silicones produced by Dow-Corning, Midland, Mich. Polydimethylsiloxanes having viscosities between about 350 centistokes and about 1,000,000 centistokes are used as lubricants in medical devices. For particular applications, any silicone compound falling substantially within this range of viscosities is considered within the scope of the present invention.

For reference, a table relating the gauge size of needle tubing to the outside diameter in mm is given. Generally epidural needles range from about 16 gauge to about 20 gauge. For illustrative purposes, the examples given are 20 gauge needles. The gauge size used in the examples is not to be considered limitative to 20 gauge, other sizes, both larger and smaller are considered to be within the scope of the present invention.

Table of Hypodermic Tubing

| Nominal Sizes (Gauge) | Outside Diameter (mm) |
|---|---|
| 30 | 0.30 |
| 29 | 0.33 |
| 28 | 0.36 |
| 27 | 0.40 |
| 26 | 0.46 |
| 25 | 0.51 |
| 24 | 0.56 |
| 23 | 0.64 |
| 22 | 0.71 |
| 21 | 0.82 |
| 20 | 0.90 |
| 19 | 1.08 |
| 18 | 1.27 |
| 17 | 1.50 |
| 16 | 1.65 |

In the Examples, the uncoated portion of the needle is selected as 2.2 cm (25 percent of the needle length) as illustrative of the invention. Other uncoated to coated percentages or differential treatments other than coatings could equally as well have been selected, and for particular applications may be preferred, and are considered to be within the scope of the invention.

EXAMPLE 1

An aqueous suspension of polytetrafluoroethylene (PTFE) particles (sized between about 2,000 to about 10,000 Angstroms, molecular weight above about 1,000,000) is prepared. Well-cleaned stainless steel needles are dipped vertically, with the point down, into the suspension until the needle is substantially completely covered. The needles are allowed to remain resident in the bath for about 5 to 10 seconds, removed and allowed to drain. The needles are then dipped, point down, in a deionized water to a preselected depth to remove the PTFE coating from the distal portion. In this example, the needle is an epidural needle size 20 gauge with an 18.9 cm length. The depth of the dip into the PTFE suspension covers substantially the entire length of the needle. The depth of the dip into the deionized water bath is 2.2 cm (25 percent). After the water dip, the needle bores are air flushed with clean dry air to clear the bores. Alternatively, the PTFE suspension may be removed from the distal portion by a controlled pattern water spray followed by air flushing the bore. The needles are rotated to a substantially horizontal position and are then maintained at a temperature between about 15° C. to about 150° C. for between about two minutes to about fifteen minutes to substantially remove the residual water from the PTFE coating remaining on the proximal portion of the needle. The PTFE coating is then fused to a substantially continuous film by exposing the proximal coated portion of the needle to a temperature between about 350° C. to about 370° C. for about one to about five seconds.

In standard penetration testing in human cadaver tissue, needles coated with fused PTFE in a process similar to that described above show a reduction in drag force to about sixty percent of the drag force observed with a dry uncoated control needle.

EXAMPLE 2

A hydrofluorocarbon solution of a curable organosilicone lubricant is prepared with a concentration of between about three to about five percent of the lubricant. Needles are positioned substantially horizontally and the needle surface is sprayed with the curable silicone solution so that the proximal portion is substantially coated and the distal portion is left substantially uncoated. In this example, the needles are 20 gauge with an 18.9 cm length. The spray pattern is controlled so that the distal portion of about 2.2 cm (twenty-five percent) is left substantially uncoated. The hydrofluorocarbon solvent selected preferably has a vapor pressure near atmospheric pressure at room temperature so that the solvent evaporates rapidly, leaving the coating to cure on the needle surface.

In standard penetration testing on human cadaver tissue, needles coated with curable silicone lubricant in a process similar to that described above show a reduction in drag force to about fifty percent of the drag force observed with a dry unlubricated control needle.

EXAMPLE 3

A hydrofluorocarbon solution of polydimethylsiloxane (silicone) with a viscosity between about 12,000 centistokes and about 13,000 centistokes is prepared with a concentration about three to about five percent (weight/weight). Needles are position substantially horizontally and sprayed with the silicone solution so that proximal portion of the needle is substantially coated and the distal portion is substantially uncoated. In this example, the needles are 20 gauge with an 18.9 cm length. The spray pattern is controlled so that the distal portion of about 2.2 cm (about twenty-five percent) is left uncoated. The hydrofluorocarbon solvent preferably has a vapor pressure near atmospheric pressure at room temperature so that the solvent evaporates rapidly, leaving the silicone lubricant on the proximal surface.

In standard penetration testing on human cadaver tissue, needles coated with silicone lubricant in a process similar to that described above show a reduction in drag force to about thirty-three percent of the drag force observed with a dry unlubricated control needle.

The examples and the penetration testing results show the reduced drag of lubricated needles when compared to unlubricated needle controls. The present invention substantially reduces the drag force generated by sliding friction of the proximal portion of the needle against the patient's tissue. Reduction of the drag force for passage of the proximal portion of the needle allows the practitioner to discriminate the penetration of the unlubricated distal point through the structures present in the patient's tissue more easily and enhances the ability of the practitioner to position the needle more accurately.

What is claimed is:

1. A hypodermic needle comprising:
   an elongate hollow tube with a proximal end, a distal end and a bore therethrough;
   a hub attached to said proximal end to releasably connect said needle to a fluid handling device, said distal end including a point; and
   said tube having an outside surface with a proximal portion and a distal portion wherein said proximal portion has a lubricative coating thereon, said distal portion having a higher coefficient of sliding friction with a patient's tissue than said proximal portion.

2. The needle of claim 1 wherein said distal portion comprises between about one percent to about forty percent of said outside surface of said tube.

3. A hypodermic needle comprising:
   an elongate hollow tube with a proximal end, a distal end and a bore therethrough;
   a hub attached to said proximal end to releasably connect said needle to a fluid handling device, said distal end having a sharp point for facilitating penetration of said needle into a patient's tissue; and
   said tube having an outside surface with a lubricated proximal portion and an unlubricated distal portion, said unlubricated distal portion enabling a practitioner to discriminate said needle's penetration of structures in the patient's tissue and said lubricated portion reducing a drag force for passage of said proximal portion through the structures already penetrated.

4. The needle of claim 3 wherein said distal portion comprises between about one percent to about forty percent of said outside surface of said tube.

5. The needle of claim 3 wherein said distal portion comprises about ten percent of said outside surface of said tube.

6. The needle of claim 3 wherein said needle is an epidural needle having a length between about five to about twenty centimeters.

7. The needle of claim 6 wherein said distal point comprises an oval opening to said bore formed in said tube at an angle to a longitudinal axis of said elongate tube so that said tube forms a sharp distal point.

8. The needle of claim 3 wherein said needle has an outside diameter between about 0.7 mm to about 1.5 mm.

9. The needle of claim 3 wherein said outside surface of said tube further includes a plurality of markings for indicating the depth of penetration of said needle into a patient's tissue.

10. The needle of claim 3 wherein said lubricated portion has a coating comprising a material that reduces the coefficient of sliding friction between the surface of the needle and a patient's tissue below the coefficient of sliding friction between the surface of the unlubricated portion of the needle and the patient's tissue.

11. The needle of claim 10 wherein said coating of said lubricated portion comprises organic silicone.

12. The needle of claim 10 wherein said coating of said lubricated portion comprises polytetrafluoroethylene.

13. The needle of claim 12 wherein said coating of said lubricated portion comprising polytetrafluoroethylene is between about 0.5 microns to about 3 microns thick.

14. A hypodermic epidural needle comprising:
   an elongate hollow tube having an outside surface and a longitudinal axis, said tube having a proximal end, a distal end and a bore therethrough;
   a hub fixedly attached to said proximal end of said tube to releasably connect said needle to a fluid handling device, said distal end having a substantially oval opening into said bore at an angle to said axis to form a sharp point for facilitating penetration of said needle into a patient's tissue; and
   said tube outside surface having a lubricated proximal portion and an unlubricated distal portion, wherein said distal portion comprises between about one to about forty percent of said outside surface, said unlubricated distal portion enabling a practitioner to discriminate the needle's penetration of structures in the patient's tissue and said lubricated portion substantially reducing a drag force for passage of said proximal portion through the structures already penetrated.

15. The epidural needle of claim 14 wherein said outside surface of said tube further includes a plurality of markings for indicating the depth of penetration of said needle into a patient's tissue.

16. The epidural needle of claim 15 wherein said hub further includes a removable flange for facilitating the practitioner's advancement of said needle into the patient's tissue, said flange being substantially normal to said axis of said needle.

17. The epidural needle of claim 15 further including a removable stylet to occlude said bore.

18. The epidural needle of claim 15 including a shield to cover said distal point, said epidural needle placed in a package formed from materials substantially resistant to the passage of microorganisms and exposed to conditions capable of rendering any microorganisms therein substantially nonviable.

19. A packaged epidural needle assembly comprising:

an elongate hollow tube having an outside surface with a plurality of markings for indicating the depth of penetration of said needle into a patient's tissue and a longitudinal axis, said tube having a proximal end, a distal end and a bore therethrough;

a hub fixedly attached to said proximal end of said tube to releasably connect said needle to a fluid handling device;

a removable flange for facilitating the practitioner's advancement of said needle into the patient's tissue, said flange being positioned on said hub substantially normal to said axis of said tube, said distal end having a substantially oval opening into said bore at an angle to said axis to form a sharp point for facilitating penetration of said needle into a patient's tissue;

a removable stylet positioned within said bore to occlude said bore;

a shield positioned over said tube to cover said distal point, said tube outside surface having a lubricated proximal portion and an unlubricated distal portion, wherein said distal portion comprises between about one to about forty percent of said outside surface, said unlubricated distal portion enabling a practitioner to discriminate the needle's penetration of structures in the patient's tissue and said lubricated portion substantially reducing a drag force for passage of said proximal portion through the structures already penetrated; and a sealed package formed from materials substantially resistant to the passage of microorganisms having said epidural needle assembly therein.

* * * * *